US007068366B2

United States Patent
Burk

(10) Patent No.: US 7,068,366 B2
(45) Date of Patent: Jun. 27, 2006

(54) SIMULATED CALIBRATION SAMPLE FOR A SPECTROGRAPHIC MEASUREMENT SENSOR AND METHOD FOR USE

(75) Inventor: Gary Neil Burk, Powell, OH (US)

(73) Assignee: ABB Inc., Columbus, OH (US)

( * ) Notice: Subject to any disclaimer, the term of this patent is extended or adjusted under 35 U.S.C. 154(b) by 423 days.

(21) Appl. No.: 10/698,566

(22) Filed: Oct. 31, 2003

(65) Prior Publication Data

US 2005/0094139 A1     May 5, 2005

(51) Int. Cl.
*G01J 3/00*     (2006.01)
*G01N 21/93*    (2006.01)
(52) U.S. Cl. .................................. 356/300; 356/243.1
(58) Field of Classification Search ................. 356/300, 356/326, 328, 243.1, 243.4, 243.5, 243.8
See application file for complete search history.

(56) References Cited

U.S. PATENT DOCUMENTS 6,960,769 B1 *  11/2005  Burk et al. ............ 250/339.07

* cited by examiner

*Primary Examiner*—F. L. Evans
(74) *Attorney, Agent, or Firm*—Stevens & Showalter LLP

(57) ABSTRACT

A simulated calibration and verification reference sample for a measurement system including a blackbody radiation source and a spectrographic sensor is disclosed. By providing a simulating reference sample, no actual sample is required and the problems associated with an actual sample including preparation, maintenance, use, storage, replacement and the like are eliminated.

10 Claims, 2 Drawing Sheets

SIMULATED CALIBRATION SAMPLE FOR A SPECTROGRAPHIC MEASUREMENT SENSOR AND METHOD FOR USE

The invention of the present application relates in general to reference samples for calibration of spectrographic measurement sensors used to measure constituents of flat sheet products, for example webs of material as they are being manufactured, and more particularly, to a simulated reference sample for calibration of spectrographic measurements and a method for using a simulated reference sample. While the present invention is generally applicable for spectrographic measurement of a variety of materials including a wide variety of material webs, it will be described herein primarily with reference to spectrographic measurement of a paper web as it is being manufactured for which it is particularly applicable and initially being used.

BACKGROUND OF THE INVENTION

During the manufacture of flat sheet products, such as paper, plastic films, textiles, and the like, incandescent or blackbody light sources and corresponding sensors are used in measurement systems to measure constituents of a quickly moving, fluttering product web. For use with a web-manufacturing machine, measurement systems are often mounted on measurement platforms that support the light sources on one side of the web and the sensors on the other side of the web. Such sensors can also be configured in a reflection mode rather than a transmission mode. In reflection mode sensors, light sources and sensors are mounted on the same side of the web and may be mounted in a common housing. In any event, the measurement systems are scanned in a cross-process direction as the web moves relatively rapidly in a process direction. The scanning platforms are arranged so that they can move the light sources and sensors "off-sheet", i.e., beyond at least one edge of the web product, so that an air gap is located between or adjacent to the light sources and sensors. While reflection sensors can be calibrated on-sheet, the light sources and sensors of both transmissive and reflective devices can be tested, serviced and calibrated while they are off-sheet.

Spectrographic sensors (also known as spectroscopic sensors) are common measuring devices used for measurement systems associated with web-manufacturing machines. In these applications, spectrographic sensors measure radiation transmitted through a web at specific wavelengths or wavelength bands with measurements indicating the presence or absence of different materials and, if present, the amount of the materials within the web. Exemplary materials that the sensors may measure include water, polymers, cellulose and other components of the web. A common application is the measurement of the fraction of water by weight (percent moisture) in a moving paper web during manufacturing.

Conventionally, a sensor is initially standardized with nothing between the light source and sensor so that variations in the source and measurement system can be accommodated. Then, to calibrate, test and/or verify that an infrared spectrographic sensor is performing properly, a standard physical sample, having stable, known properties, is inserted in place of the web product being manufactured. The sensor readings with the standard sample are recorded and compared with the known value of those properties of the standard sample. The sensor parameters or calibration factors conventionally stored in look-up tables or other memory devices are adjusted until the sensor readings conform to the known values of the standard sample. To provide automated testing and/or verification, a standard sample may be internal to the measurement system and automatically inserted in place of the web, increasing the complexity of the measurement system. With an internal standard sample in place, a sensor measurement is taken and a check or automated calibration is performed for the sensor.

Unfortunately, the construction and maintenance of standard samples can be problematic. Initially, the standard sample must adequately simulate the properties of the web product that the sensor is measuring and the properties of the standard sample that serve as the basis for tests and/or calibrations must be extremely stable. Once such a sample is prepared, it must be able to remain stable and not be destroyed or damaged while being used and stored in the full range of harsh manufacturing environments that web-manufacturing may encounter including, for example, high humidity, dirt, heat and water in the case of paper manufacturing. Further, the sample must be able to withstand exposure to the light source itself which, when concentrated for testing, standardization and/or calibration, may be intense and tends to alter the properties of the sample. To meet these requirements, the standard sample may need to be protected for example by placement in a special storage environment between uses.

Further, if the standard sample becomes lost, contaminated, aged, damaged or otherwise unavailable, it may be expensive and time consuming to replace the standard sample. And, until the standard sample is replaced, the sensor may not be able to be calibrated or have readings verified except by laborious preparation of short-lived samples at the web-manufacturing facility.

Accordingly, there is a need for a calibration and verification reference sample for a measurement system including a blackbody radiation source and a spectrographic measuring device that overcomes or lessens these problems.

SUMMARY OF THE INVENTION

This need is met by the invention of the present application wherein a simulated calibration and verification reference sample for a measurement system including a blackbody radiation source and a spectrographic sensor is provided. By simulating a reference sample, no actual sample is required and the problems associated with an actual sample including preparation, maintenance, use, storage, replacement and the like are eliminated.

BRIEF DESCRIPTION OF THE DRAWINGS

The benefits and advantages of the present invention will become apparent to those skilled in the art to which this invention relates from the subsequent description of the illustrated embodiments and the appended claims, taken in conjunction with the accompanying drawings, wherein:

DETAILED DESCRIPTION OF THE INVENTION

Figure 1:
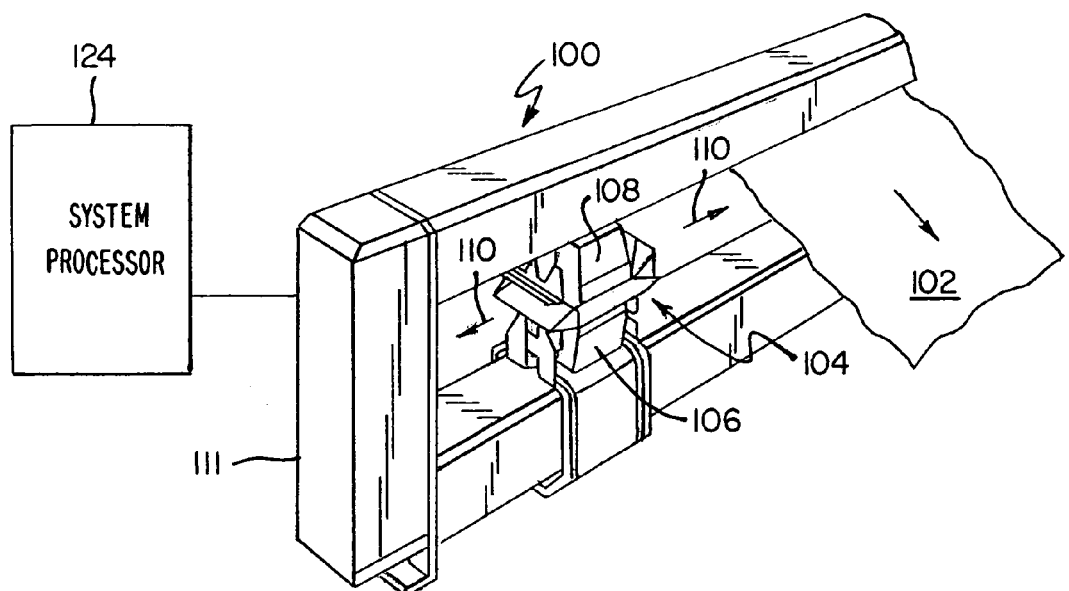
FIG. 1 is a diagram illustrating a monitoring station of a paper web-manufacturing machine including the invention of the present application.

While the present invention is generally applicable to any web manufacturing process, it will be described herein with reference to paper manufacturing for which it is particularly applicable and initially being used. Referring now to the drawings, in which like-referenced characters indicate corresponding elements throughout the drawings, attention is first drawn to FIG. 1 that shows a web monitoring station 100 of a paper web-manufacturing machine (not shown) with the station 100 including the invention of the present application. The paper-manufacturing machine produces a paper web 102 and the web monitoring station 100 includes a sensor system 104 comprising a light source housing 106 and a light detector housing 108. It is to be appreciated that both the source housing 106 and the detector housing 108, as illustrated, are mounted for conventional scanning back and forth across the web 102 in a cross-machine direction (CD), as shown by the arrows 110, using a measurement platform 111.

Figure 2:
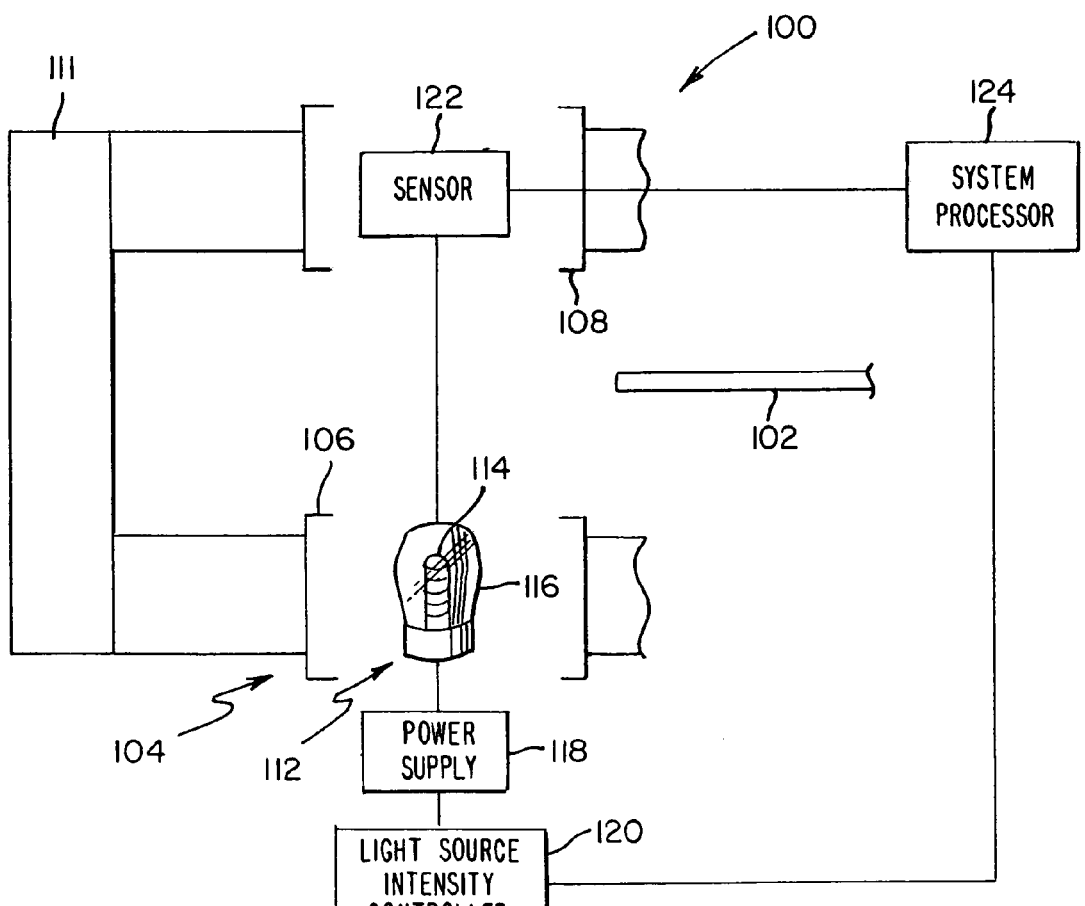
FIG. 2 is a schematic diagram illustrating the internal structure of sensor elements of the monitoring station of FIG. 1.

Referring now to FIG. 2, mounted inside the source housing 106 is a lamp 112 having a filament 114 and a protective globe 116. The filament 114 may be a tungsten filament and may have a length of about 3.8 mm and a diameter of about 1.95 mm. The protective globe 116 may be formed of glass which may be covered with a reflective coating and may enclose a gas, such as halogen gas, as is conventional. Coupled to the lamp 112 are a power supply 118 and a light source intensity controller 120. The power supply 118 can be varied between, for example, outputs of zero volts and ten volts. The light source intensity controller 120 includes conventional electronics necessary to regulate and vary the voltage supplied by the power supply 118 to the lamp 112. Mounted inside the detector housing 108 is a spectrographic sensor 122. The spectrographic sensor 122 is connected to a system processor 124 that includes conventional electronic devices and systems needed for signal processing and other functions.

The lamp 112 generates a broad bandwidth light or white light signal having a light intensity that is controlled by the level of the voltage applied to the lamp 112. The lamp 112 emits high energy density light including multiple infrared wavelengths onto a focal spot of about one centimeter in diameter at a controlled focal distance. The lamp 112 may be air-cooled using an air shroud (not shown) or otherwise cooled to increase lamp life and to reduce heat effects on the sensor system 104.

Figure 3:
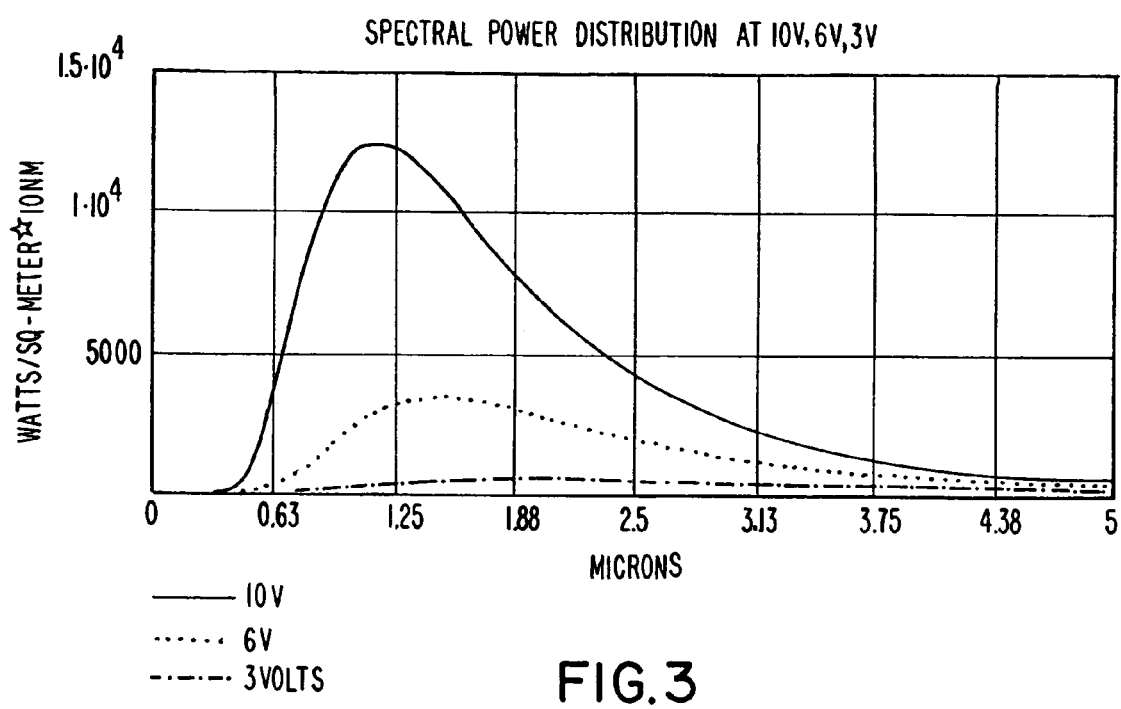
FIG. 3 is a graph of varying power spectral densities for use in the present invention.

As the voltage to the lamp 112 is varied, the spectral distribution of the light output shifts as predicted by Planck's Law for Blackbody Radiation. As is known, a higher voltage emits more radiation and the peak wavelength shifts to a shorter wavelength while a lower voltage emits less radiation and the peak wavelength shifts to a longer wavelength as is shown in FIG. 3 which illustrates how the spectral power distribution varies as the voltage to the lamp 112 is controlled to be at three different voltages, 10.0 volts, 6.0 volts and 3.0 volts. At 10.0 volts, the peak wavelength is about 1.168 μm, while at 6.0 volts, the peak wavelength is about 1.508 μm, and at 3.0 volts, the peak wavelength is about 2.132 μm. Therefore, when the voltage provided to the filament 114 is controlled, the spectral power distribution of the filament 114 is likewise controlled so that when the voltage is increased to the lamp 112, the lamp 112 output becomes "whiter" in addition to becoming brighter.

When operating the sensor system 104 to measure web constituents or characteristics, light from the lamp 112 is projected onto a small area of the paper web 102. As shown in FIG. 2, the sensor system 104 is off-sheet and in a position that can be used for sensor validation, testing, calibration and the like. The constituents of the paper web 102 interact with the incident light and absorb or transmit various spectral components of the light so that those constituents of the web can be measured. The constituents or characteristics being measured may include any properties with specific and discrete absorption bands, such as moisture, polymers, cellulose, and the like.

The spectrographic sensor 122 measures light over different bands of wavelengths and outputs corresponding voltages. Spectrographic sensor 122 may include a plurality of detector elements to detect different wavelengths or bands of wavelengths or a plurality of spectrographic sensors may be included to detect different wavelengths or bands of wavelengths. Each specific wavelength or band corresponds to a component or characteristic of interest in a product web, such as paper, plastic film or the like, and the sensors/detectors determine the spectral absorption properties for the product.

As is well known in spectrographic measurement, the spectrographic sensor 122 operates by measuring and determining the relative absorption of various wavelengths of different constituents of the paper web 102. For example, a first wavelength is measured where absorption by a constituent of interest is high. Then a second, nearby wavelength is measured where absorption by the constituent of interest is low. A function of the ratio of the radiation transmitted through the web product is proportional to the weight or amount of the constituent in the web. Thus, for each measured constituent, these ratio functions create a unique "fingerprint" or pattern. As the constituent content or other optical properties of the web vary, the relative absorptions also vary. For each measured constituent, the measuring application is designed to maximize the sensor sensitivity to changes in that constituent and to minimize the sensor sensitivity to other constituent and optical changes.

As shown in FIG. 2, the lamp 112 and the sensor 122 may be operated off the sheet of material (without the web product being present in the web monitoring station 100 between the lamp 112 and the sensor 122). In the off-sheet position, conventionally a sensor was initially standardized, normally with nothing between the light source and sensor, so that variations in the lamp 112 and the sensor 122 can be accommodated by the sensor system 104. Once the sensor system 104 was standardized, a standard sample was manually or automatically inserted in the gap between the lamp 112 and the sensor 122, measurements were taken and ratio functions determined to see whether readings for the sensor 122 were accurate. If not, calibration parameters were determined based on the known characteristics of the standard sample so that the readings of the sensor 122 could be modified in accordance with the calibration parameters so that sensor readings were accurate.

In accordance with the present invention, there is no actual standard sample, rather, a simulated standard sample is provided. The light source intensity controller 120 is controlled to set the voltage supplied by power supply 118 to the lamp 112 to at least two different voltages within the available range of the power supply 118. The first voltage is used to standardize the sensor, as before with nothing in the gap between the lamp 112 and the sensor 122, and the second voltage is used to calibrate the sensor, so that the second voltage provided to the lamp 112 shifts the output of the lamp 112 to simulate the presence of an actual standard sample.

For example, a first voltage may be selected as 10 volts and a second voltage may be selected at 6 volts. With 10 volts applied to the lamp 112, the resulting light from the lamp 112 illuminates the sensor 122 and measurements are taken at a wavelength of interest and a reference wavelength. For example, for moisture, a peak absorption wavelength is typically about 1.95 μm. The reference wavelength is selected to be the shortest wavelength that is sensed by the sensor 122, for example ~1.85 μm, of course this is dependent upon the sensor and other reference wavelengths can be used in the present invention. The ratio between the sensor signal at the wavelength of interest and sensor signal at the reference wavelength is determined and used to standardize the sensor 122, i.e., for example, if the sensor signal of interest is X volts and the sensor signal at the reference wavelength is Y, then X/Y provides a standardization ratio that is applied to the sensor signal for measurements of the wavelength of interest.

With the second voltage, 6 volts for example, applied to the lamp 112, the resulting light from the lamp 112 is shifted as illustrated in FIG. 3, and illuminates the sensor 122. Measurements are again taken at the wavelength of interest and the reference wavelength. The ratio between the sensor signal at the wavelength of interest and the sensor signal at the reference wavelength is taken and used to calibrate the sensor 122. For example, if the standardization ratio X/Y no longer produces accurate readings from the sensor, that ratio is adjusted to provide the proper calibration. The inventor of the present application has determined that the ratio of different wavelengths for different voltages applied to the lamp 112 will remain constant over time even as the output of the lamp 112 changes with age.

Accordingly, standardization of the sensor 122 is performed with nothing in the gap between the lamp 112 and the sensor 122, the same as when an actual standardized sample was used. Then, the light provided by the lamp 112 is changed (as if an actual sample was inserted between the lamp 112 and the sensor 122) and calibration is performed based on the changed light provided by the lamp 112, again with nothing in the gap between the lamp 112 and the sensor 122. By changing the light provided by the lamp 112, and hence received by the sensor 122, which is the same thing that happens when an actual sample is inserted into the gap between the lamp 112 and the sensor 122, a simulated sample is provided. Knowing that the ratios of different wavelengths will be the same over time, i.e., as the lamp 112 ages, the calibration is consistent and no actual sample is required.

The first standardization voltage and the second calibration voltage can be selected between a value greater than zero, which provides adequate light for a meaningful measurement, and a maximum voltage, for example in the illustrated embodiment, a value equal to or less than ten volts. A larger difference between the two voltages provides more accuracy when using the simulated sample. Additional discrete voltages can also be used to generate additional data for canceling out typical measurement errors in the system.

The changes in the source spectrum can be selected to exercise virtually all of the wavelengths of the sensor 122 and the changes in the source spectrum can be selected to fairly closely exercise the wavelengths of a particular web constituent of interest. For example, as previously noted, at 10.0 volts, the peak wavelength is about 1.168 μm, while at 6.0 volts, the peak wavelength is about 1.508 μm, and at 3.0 volts, the peak wavelength is about 2.132 μm. Thus, if the moisture content of a web product is the constituent desired to be measured, the simulated calibration sample may use a voltage that generates a peak wavelength near the peak absorption wavelength of moisture, typically about 1.95 μm.

The elimination of the physical reference sample eliminates errors caused by changes in the sample's physical characteristics such as changes in moisture content, temperature, color, etc., as well as complexity in design to utilize the physical reference sample.

Although the above-described embodiment illustrates a simulated calibration and/or verification reference sample for use in a spectrographic measurement system for manufacturing a web product, it will be obvious that the present invention can be used in any measurement system using a blackbody radiation source and a spectrographic sensor. Obviously, a plurality of blackbody radiation sources and/or spectrographic sensors can be used in accordance with the present invention.

Although the invention has been described with particular reference to certain illustrated embodiments thereof, variations and modifications of the present invention can be effected within the spirit and scope of the following claims.

What is claimed is:

1. A method for operating a measuring sensor having a radiation source and a spectrographic sensor comprising:
   operating said radiation source to generate a first light signal having a first spectral power distribution;
   measuring said first light signal with said spectrographic sensor;
   generating standardization parameters based on a ratio of light sensed around a wavelength of interest and a reference wavelength;
   operating said radiation source to generate a second light signal having a second spectral power distribution; and
   measuring said second light signal with said spectrographic sensor;
   generating calibration parameters based on a ratio or light sensed around said wavelength of interest and said reference wavelength.

2. A method for operating a measuring sensor as claimed in claim 1 further comprising selecting said first light signal and said second light signal to control resolution of said calibration parameters.

3. A method for operating a measuring sensor as claimed in claim 2 wherein operating said radiation source comprises applying a voltage to a lamp, and selecting said first light signal and said second light signal comprises controlling the voltage level applied to said lamp so that a first voltage level defines said first light signal and a second voltage level defines said second light signal wherein the greater the separation between said first and second voltage levels the greater the resolution of said calibration parameters.

4. A method for calibrating a measuring sensor having a radiation source and a spectrographic sensor comprising:
   controlling said radiation source to generate a standardization light signal;
   standardizing said spectrographic sensor based on measurements of said standardization light signal taken by said spectrographic sensor;
   controlling said radiation source to generate a calibration light signal; and
   calibrating said standardized spectrographic sensor based on measurements of said calibration light signal taken by said spectrographic sensor.

5. A method for calibrating a measuring sensor as claimed in claim 4 wherein standardizing said spectrographic sensor comprises generating standardization parameters based on a ratio of said measurements of said standardization light signal made around a wavelength of interest and around a reference wavelength.

6. A method for calibrating a measuring sensor as claimed in claim 5 wherein calibrating said standardized spectrographic sensor comprises generating calibration parameters based on a ratio of said measurements of said calibration light signal made around said wavelength of interest and around said reference wavelength.

7. A method for simulating a reference sample in a measuring sensor having a radiation source and a spectrographic sensor comprising:
  varying the intensity of said radiation source to at least two intensity levels;
  measuring radiation emitted from said radiation source with said spectrographic sensor at said at least two intensity levels;
  standardizing said measuring sensor based on measurements made at a first one of said at least two intensity levels of said radiation source; and
  calibrating said measuring sensor based on measurements at a second one of said at least two intensity levels of said radiation source.

8. A method for simulating a reference sample as claimed in claim 7 wherein standardizing said measuring sensor comprises generating standardization parameters based on a ratio of said measurements made at a first one of said at least two intensity levels around a wavelength of interest and around a reference wavelength.

9. A method for simulating a reference sample as claimed in claim 8 wherein calibrating said measuring sensor comprises generating calibration parameters based on a ratio of said measurements made at a second one of said at least two intensity levels around said wavelength of interest and around said reference wavelength.

10. A simulated reference sample for a measuring sensor, said sample comprising:
  a radiation source;
  a variable power supply for driving said radiation source, said radiation source generating a first radiation having a first spectral power distribution when a first voltage is supplied to said radiation source and a second radiation having a second spectral power distribution when a second voltage is supplied to said radiation source;
  a spectrographic sensor generating first signals representative of a wavelength of interest and a reference wavelength in response to said first radiation and second signals representative of said wavelength of interest and said reference wavelength in response to said second radiation; and
  a system processor for determining a first function from the ratio of said signals representative of said wavelength of interest and said signals representative of said reference wavelength in response to said first radiation, said first ratio function being used to standardize said measuring sensor, and for determining a second function from the ratio of said signals representative of said wavelength of interest and said signals representative of said reference wavelength in response to said second radiation, said second ratio function being used to calibrate said measuring sensor.

* * * * *